(12) United States Patent
Cummins et al.

(10) Patent No.: US 8,012,511 B1
(45) Date of Patent: *Sep. 6, 2011

(54) ACIDIC COMPOSITION OF MATTER FOR USE TO DESTROY MICROORGANISMS

(75) Inventors: Barry W. Cummins, Butler, KY (US); David H. Creasey, Splendora, TX (US)

(73) Assignee: Contact Marketing Solutions, LLC, Danbury, CT (US)

( * ) Notice: Subject to any disclaimer, the term of this patent is extended or adjusted under 35 U.S.C. 154(b) by 1597 days.

This patent is subject to a terminal disclaimer.

(21) Appl. No.: 11/293,535

(22) Filed: Dec. 2, 2005

(51) Int. Cl.
| | |
|---|---|
| A01N 59/00 | (2006.01) |
| A01N 59/02 | (2006.01) |
| A01N 59/06 | (2006.01) |
| A01N 59/16 | (2006.01) |
| A01N 59/20 | (2006.01) |
| A01N 59/26 | (2006.01) |
| A01N 37/02 | (2006.01) |
| A01N 37/06 | (2006.01) |
| A61K 33/02 | (2006.01) |
| A61K 33/04 | (2006.01) |
| A61K 33/24 | (2006.01) |
| A61K 33/30 | (2006.01) |

(52) U.S. Cl. ........ 424/604; 424/606; 424/617; 424/637; 424/638; 424/639; 424/641; 424/642; 424/697; 424/703; 424/709; 424/710; 424/713; 424/719; 424/720; 514/557; 514/574; 514/886; 514/887

(58) Field of Classification Search .................. 424/637, 424/641, 642, 697, 703, 709, 710, 713, 606, 424/617, 638, 639, 719, 720; 514/557, 574, 514/886, 887
See application file for complete search history.

(56) References Cited

U.S. PATENT DOCUMENTS

| | | | | |
|---|---|---|---|---|
| 3,919,416 A | | 11/1975 | Cosby | 424/710 |
| 3,923,983 A | | 12/1975 | Pensack | 424/709 |
| 4,116,664 A | | 9/1978 | Jones | 71/29 |
| 4,310,343 A | | 1/1982 | Verdegaal et al. | 71/28 |
| 4,402,852 A | | 9/1983 | Young | 71/28 |
| 4,404,116 A | | 9/1983 | Young | 71/28 |
| 4,445,925 A | | 5/1984 | Young | 71/28 |
| 4,564,504 A | | 1/1986 | Sorber | 422/189 |
| 4,673,522 A | | 6/1987 | Young | 134/19 |
| 4,776,963 A | | 10/1988 | Inagaki et al. | 210/764 |
| 4,817,333 A | | 4/1989 | Szepessy et al. | 47/58.1 |
| 4,996,333 A | * | 2/1991 | Berg | 549/328 |
| 5,185,151 A | | 2/1993 | Young | 424/400 |
| 5,989,595 A | | 11/1999 | Cummins | 424/710 |
| 6,242,011 B1 | * | 6/2001 | Cummins | 424/710 |
| 6,565,893 B1 | * | 5/2003 | Jones et al. | 424/616 |
| 7,192,618 B2 | * | 3/2007 | Cummins et al. | 426/321 |

OTHER PUBLICATIONS

Medline abstract 2002222378 (2002).*
Medline abstract 1991059277 (1991).*
Saito, K. et al., "Thermal decomposition of ethyl acetate . . . " Chemical Physics Letters, vol. 170(4), 1990; abstract only.*

* cited by examiner

Primary Examiner — John Pak
(74) Attorney, Agent, or Firm — Brian S. Steinberger; Law Offices of Brian S. Steinberger, P.A.

(57) ABSTRACT

A composition of matter and the method of making that provide a low pH acidic composition that is useful for destroying microorganisms that are undesirable and useful for destroying or reducing melanoma on human skin. The composition and method include a strong, low pH acid combined with distilled water and urea or an ammonium compound, such as ammonium sulfate or other metallic sulfates, including but not limited to, sodium sulfate, magnesium sulfate, zinc sulfate, manganese sulfate, and copper sulfate, under at least 15 psi pressure in pressurized container, all of which is heated to approximately 800° F. or more for at least 3 hours. The final cooled mixture is stabilized with 10 to 15 percent of the original mixture. The resultant composition is useful for preserving food, such as fresh fish, and for skin treatment of melanoma and as bactericides, fungicides, or viricides.

9 Claims, No Drawings

ACIDIC COMPOSITION OF MATTER FOR USE TO DESTROY MICROORGANISMS

FIELD OF THE INVENTION

This invention relates to a composition of matter and the method of making improved acidic compositions that are useful for the treatment of killing bacteria or other potentially toxic cells, including diseases cells, and specifically to an improved composition of matter and the method of making that can be used as a bactericide, fungicide, viricides, and for the treatment of skin diseases.

BACKGROUND AND PRIOR ART

The use of acids and acidic chemicals for killing deleterious organic organisms, such as bacteria, germs, and viruses is well known in the art. Chlorine or hydrochloric acid is especially useful as a bactericide and is used universally as a cleaning agent.

Bacteria play an important role in the deterioration of human foodstuffs. Foods such as fish are particularly susceptible to rapid deterioration, especially at room temperature, and compounds for the preservations of foods or the retardation of bacteria growth have been employed in the past. One of the problems with such compounds is that in certain increased levels, they can be toxic to human beings, thereby defeating the purpose of preserving the foodstuffs.

Because of the extremely acidic nature of some of the bactericides and viricides that have been utilized in the past, oftentimes they can cause skin irritation or other side effects for human begins coming in contact with these compositions, or can even be fatal if accidentally consumed. Chlorine has had other negative implications in terms of the environment, and has not been environmentally friendly because of the release of chlorine gas into the environment.

The present invention provides for a composition of matter and the method of making it that produces a composition that operates in a very low pH range to provide toxicity to bacteria, viruses, and certain malignant cells that attack human skin dermatologically, while at the time proving to be nontoxic to human beings and not harmful to healthy human cells.

The use of the invention has been found to be helpful as a bactericide for preserving fresh food items, such as fish, for long periods of time without toxically endangering the food product, and has also been found useful as a dermatological composition to reduce or eliminate melanoma of the skin as a skin care product.

In U.S. Pat. Nos. 5,989,595 and 6,242,011 B1 to Cummins, an acidic composition of matter is disclosed that is useful for destroying microorganisms that spoil food, such as fish. The composition of matter, patented by Cummins, is expandable to include additional reactants that provide a very low pH acidic composition that is nontoxic to human beings and not harmful to healthy human cells.

Headlines in 2005 regarding the avian flu in various countries and the threat of a global pandemic encourages consideration of the use of the acidic, non-toxic composition of the present invention to decrease the concentration of ammonia gases in open chicken pens. The ammonia gas, from chicken waste, acts as an irritant to the lungs of the fowl making them vulnerable to infection by the deadly virus that causes avian flu. The present invention can provide a two-fold benefit for chickens or fowl in open pens. First, by converting ammonia to a harmless salt, the free ammonia gas no longer irritates the lungs of penned birds; the birds will have a stronger immune system and will be less susceptible to the flu virus. Second, when ammonia is converted to a harmless salt, the feet pads of the birds or fowl will not have chemical ammonia burns causing the birds to become inactive and develop pneumonia from inactivity.

SUMMARY OF THE INVENTION

A primary objective of this invention to provide an improved composition of matter that has desirable acidic (low pH) characteristics that are not harmful or deleterious to organic human cells to destroy microorganisms or in the treatment of skin diseases.

A second objective of this invention to provide an improved composition of matter and the method of making it to create a widely usable composition for bactericide, fungicide, and complete elimination and destruction of microorganisms that are toxic to human health.

A third objective of this invention is to create a composition of matter that has numerous applications in areas of bactericide, viricide, food preservation, and dermatological treatment of human skin cells to eliminate or reduce diseases of the skin.

A fourth objective of the present invention is to provide a method for making an improved low pH acidic composition of matter that is not harmful or deleterious to organic human cells and can destroy microorganisms.

A fifth objective of the present invention is to provide a non-toxic, low pH, acidic composition of matter that can be applied to open pens containing birds or fowl and convert free ammonia gas from fowl waste to a harmless salt thereby improving the conditions in such open pens so that the fowl are less susceptible to the avian flu virus.

A composition of matter formed by the following described method has been found to be an effective bactericide, fungicide, viricide, and low pH acidic composition that is nontoxic to healthy human cells.

The first basic ingredient used is a strong or low pH acid, preferably food grade and of at least 98 percent purity. The acid is placed in a container in a predetermined quantity. The next step is to place water, preferably distilled water or a better quality of water, such as pharmaceutical or medical grade, in a separate container and heat said water to 140° F., at which time 2.77 lbs. per gallon of 21 percent active ammonium compound or metallic sulfate is added to the water using a 316 L stainless tube to inject air or use a mechanical mixer, to dissolve the ammonium compound, urea or metallic sulfate in the $H_2O$.

The mixture of low pH acid, water, and ammonium compound, urea or metallic sulfate are themselves injected simultaneously at the predetermined ratio into a pressure vessel, preferably made of stainless steel, the volume of which is significantly larger than the total of composition to be obtained. The overall mixture is sprayed by nozzles into the pressure vessel, which is maintained at pressure ranges between approximately 1 psi to approximately 20 psi above atmospheric pressure, preferably in a range between 2 psi and 7 psi above atmospheric pressure.

At approximately the 1 ft. of liquid level, a plurality of electrodes are disposed to contact the liquid as it fills the pressure vessel, with a predetermined amount of DC current (amperage) provided. The positive and negative electrodes are spaced approximately 3 ft. apart. A DC voltage and current of at least one amp is provided. High pressure air is also forced into the liquid from radially disposed radial pipes to cause the overall mixture to rotate vigorously within the pressure vessel.

The pressure vessel will also include a cooling jacket. The temperature of the mixture is heated not to exceed 1200° F. and kept at this temperature for 3 to 4 hours. The pressure vessel permits release of gas, which is believed to be hydrogen gas, coming off the mixture.

The mixture is then cooled down to room temperature, at which time a stabilizer, which is 10 percent of total weight of the original mixture, is introduced into the cool down mixture. The overall composition of the matter is then ready for use, either as a fresh food preservative, or can be implemented with various skin creams that are carriers for use in dermatology for reducing or eliminating melanoma on human skin.

For use as a food preservative, the composition of the matter is coated over items such as fresh fish, with the composition acting as bacteria retardant.

The pressure vessel may be made of stainless steel, as are the electrodes used therein.

When urea is used as a reactant, the ammonium sulfate mixture is replaced by a 46 percent urea substitute, with the methodology being the same as for the ammonium sulfate composition.

The composition arrived at may be diluted down further, depending on the particular use, with additional distilled water, much like a typical acid. Applicant has found that although the pH is low (below 2), the composition is not deleterious or toxic to healthy human cells, and does not cause irritation to humans when coming in contact with the acidic composition.

A preferred composition of matter that is not an irritant or deleterious to humans, is prepared by combining a strong, low pH acid with water and an ammonium compound to provide mixture (I), combining the mixture (I) in a pressurized vessel and heating the mixture, cooling the mixture, and after the mixture is cooled, adding a stabilizer to mixture (I). Preferably, the mixture (I) is heated, then stirred vigorously by air or mechanical mixer under pressure in the pressurized vessel. Preferably, the mixture is introduced under pressure into the pressurized vessel by spraying into the vessel.

The acid used in the present invention is preferably of approximately 98% purity and is at least one of sulfuric acid, phosphoric acid, fumaric acid and acetic acid.

The water used in the present invention is preferably distilled water, deionized water, filtered water, pharmaceutical grade water and medical grade water. It is also preferable that the acid chosen for the present invention be combined in an approximately 1 to approximately 2 gallon ratio with the water.

The ammonium compound used in the present invention is preferably anhydrous ammonia, ammonium sulfate, and buffered ammonium nitrate. It is most preferred that the ammonium compound is combined at a ratio of approximately 2.77 lbs of the ammonium compound per gallon of water.

In the preferred process for making the low pH acidic composition of the present invention, mixture (I) is added to a pressure vessel that is pressurized to approximately 15 psi above atmospheric pressure and then heated to at least approximately 800 degrees Fahrenheit for less than or equal to approximately 30 minutes. Thereafter the heated mixture is cooled prior to adding the stabilizer in an amount of approximately 10 weight percent of the total weight of mixture I. The stabilizer is preferably an amount of the unprocessed mixture (I).

Another preferred composition of matter that is not an irritant or is deleterious to humans is made by combining strong, a low pH acid with water and urea to provide a mixture (II) and processing as described above for mixture (I). The stabilizer is preferably an amount of the unprocessed mixture (II).

A more preferred composition of matter that is not an irritant or is deleterious to humans is made by combining strong, a low pH acid with water and a metallic sulfate to provide a mixture (III) that is processed as described above for mixture (I). The stabilizer is preferably an amount of the unprocessed mixture (III). The preferred metallic sulfate is sodium sulfate, magnesium sulfate, zinc sulfate, manganese sulfate, and copper sulfate.

The preferred low pH acid is selected from the group consisting of sulfuric acid, phosphoric acid, fumaric acid, and acetic acid.

The preferred water is selected from the group consisting of distilled water, deionized water, filtered water, pharmaceutical or medical grade water.

A preferred method of preparing a composition of matter that is not an irritant or is deleterious to humans includes preparing a strong, low pH acid in a first container, heating water, mixing an ammonium compound, urea, or metallic sulfate in said heated water, simultaneously combining the mixture of the low pH acid, heated water, and at least one of an ammonium compound, urea, or metallic sulfate (mixture III) into a separate pressurized vessel, heating the pressurized mixture and cooling said mixture and adding a stabilizer to cooled mixture.

The preferred acid is of approximately 98% purity and is sulfuric acid, phosphoric acid, fumaric acid, and acetic acid.

The preferred water is distilled water, deionized water, filtered water, pharmaceutical or medical grade water.

More of the preferred reactants are an ammonium compound, more preferably, ammonium sulfate, 46% urea substitute, anhydrous ammonia, buffered ammonium nitrate, sodium sulfate, magnesium sulfate, zinc sulfate, manganese sulfate, and copper sulfate.

The preferred process for making the low pH acidic composition of the present invention includes heating the water in a ratio of approximately twice the volume of said acid in the separate container to at least approximately 140 degrees Fahrenheit. Preferably, one reactant added to the heated water can include, an ammonium compound, urea and metallic sulfate mixed at a ratio of approximately 1 lb. to approximately 3 lbs. of the ammonium compound, urea or metallic sulfate per gallon of water.

Preferably the mixture of the acid, the heated water, and at least one of an ammonium compound, urea or metallic sulfate (mixture IV) are simultaneously combined in the separate pressurized vessel by injection and the vessel is pressurized to approximately 15 psi above atmospheric pressure, then heating to at least approximately 800 degrees Fahrenheit for at least approximately 3 hours.

A preferred further processing step includes cooling the heated mixture prior to adding the stabilizer in an amount of approximately 10 weight percent to approximately 15 weight percent of the total weight of the mixture (IV). The preferred stabilizer is an amount of mixture (IV).

A preferred non-toxic, low pH, acidic composition of matter is prepared that can be applied to an open pen containing fowl to convert free ammonia gas from fowl waste into a harmless salt thereby improving the conditions in said open pen so that the fowl are less susceptible to the avian flu virus.

Further objects and advantages of this invention will be apparent from the following detailed description of a presently preferred embodiment, which is illustrated in the examples provided herein.

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

The composition of matter provided by the present invention forms a highly effective composition to kill or retard the growth of microorganisms, especially such as bacteria, viruses, and other microorganisms.

The first basic ingredient used is a strong, low pH acid such as, sulfuric acid, phosphoric acid, fumaric acid, acetic acid and stabilized hydrochloric acid preferably of very high purity, between approximately 98 percent to approximately 99.9 percent purity. The acid is placed in a container at a predetermined quantity. The next step is to place water, preferably distilled, filtered, deionized, pharmaceutical or medical grade water in a separate container and heat said water to 140° F., at which time 2.77 lbs. per gallon of 21 percent active metallic sulfate or ammonium compound, such as, ammonium sulfate is added to the water using a 316 L stainless tube to inject air or use a mechanical mixer, to dissolve the ammonium compound in the $H_2O$.

The resultant ammonium compound or metallic sulfate, water, and acid mixtures themselves are injected simultaneously at the same ratio into a large, stainless steel pressure vessel that is maintained at a pressure of in a range between approximately 1 psi to approximately 20 psi above atmospheric pressure, preferably between approximately 2 psi and 7 psi above atmospheric pressure. The mixture is forced into the pressure vessel, which itself has positive and negative electrodes for passing a DC current through the mixture as it is filled into the pressure vessel. At least one amp of DC current is maintained approximately 1 ft. above the base of the pressure vessel.

Spargers include spray head nozzle-like spargers used to force the mixture in a spray-in form into the pressure vessel.

The reaction of acid, water and ammonium compound or metallic sulfate is an exothermic reaction. The time and temperature of the reaction will vary based on the amount of reactants, size of reactor and reactivity of selected reactants. The temperature of the mixture is preferably maintained in a range between approximately 250° F. and approximately 475° F., more preferably at approximately 350° F.±25%. If the reaction temperatures are not reached the reaction mixture is not stable, there will be strong ammonia or sulfur odors. The reaction time varies between 60 minutes and 16 hours, preferably between 3 and 8 hours, more preferably between approximately 3 to 4 hours when reactants are preheated.

Preheating is recommended with smaller volumes of reactants, between approximately 400-1000 gallons. For example, it would be advantageous to preheat ammonium sulfate so that it stabilizes at approximately 160° F., and then preheat sulfuric acid by raising the temperature from ambient temperature to approximately 125° F. before mixing these reactants, then the reaction temperature is reached quickly and maintained for a shorter period of time, such as 3-4 hours. Volumes larger than 1000 gallons do not require preheating.

A cooling jacket is required to keep the temperature below approximately 1200° F. During this process, excess gas is removed, which is believed to be hydrogen gas. A separate gas distributor is mounted within the liquid in the form of perpendicular spargers that take air and inject it into the mixture during the heating process, which causes rotation of the fluid, creating a dynamic action in which the fluid is rotating about in the pressure vessel. After approximately 4 hours, the mixture is allowed to cool down to room temperature. At the end of the cool down period, another 10 percent of the total weight of the original mixture is added to the cooled down mixture to act as a stabilizer.

The stabilizer can be added when the reaction mixture has a temperature between room temperature (approximately 70° F.) and approximately 160° F.

The resultant mixture has been found very suitable for direct use as a food preservative and for preserving food such as fish for long periods of time, up to two weeks at room temperature. When used dermatologically in a cream base, the low pH acidic composition of the present invention, has been found to reduce or eliminate skin cancers such as melanoma.

The exact chemical formula for the resultant composition is not clearly known.

Before providing specific examples of reactants and the reaction process for making the acidic composition of the present invention, the table below provides a list of a broad range of reactants that Applicant has also found to form an acidic composition with equally effective results. Table I, can be used by a person with skill in the art to make a judicious selection of one reactant from columns 1 and 2, one reactant from column 3 and one reactant from column 4.

These reactants would have a ratio within approximately ±25% to approximately ±45%, preferably within approximately 10% of the ratios discussed in the examples below. A person skilled in the art can make the appropriate adjustments within the ratios given based on the need for safety and stability of the finished product.

TABLE I

Reactants Useful in Preparing Low pH Acidic Composition

| Column 1<br>Urea or Ammonium<br>Compounds | Column 2<br>Metallic Sulfates | Column 3<br>Strong, Low pH<br>Acids | Column 4<br>Water |
|---|---|---|---|
| 46% urea substitute<br>anhydrous ammonia<br>ammonium sulfate<br>Ammonium nitrate<br>with buffers | sodium sulfate<br>magnesium sulfate<br>zinc sulfate<br>manganese<br>sulfate<br>copper sulfate | sulfuric acid<br>phosphoric acid<br>fumaric acid<br>acetic acid | distilled<br>deionized<br>filtered<br>pharmaceutical<br>or medical<br>grade |

Example 1

The first basic ingredient used is sulfuric acid, preferably of around 98 percent purity. The sulfuric acid is placed in a container at a predetermined quantity. The next step is to place distilled water in a separate container and heat said water to 140° F., at which time 2.77 lbs. per gallon of 21 percent active ammonium sulfate is added to the water using a 316 L stainless tube to inject air to dissolve the ammonium sulfate in the $H_2O$.

Simultaneously, the $H_2SO_4$, and the $H_2O$, and the ammonium sulfate $(NH_4)_2SO_4$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture, which forces the liquid mixture to dynamically rotate within the pressure vessel.

Two electrodes, a cathode and anode, provide a DC voltage 1 ft. above the bottom of the contained at approximately 1 to 3 amps, with the electrodes being 3 ft. apart.

The mixture is heated to a temperature not to exceed approximately 1200° F. and maintained at the temperature for 3 to 4 hours, during which time excess hydrogen gas is removed.

After 4 hours, the mixture is allowed to return and cool down to room temperature. After cool down, an additional 10 percent of the same mixture, is reintroduced into the original cool down mixture to act as a stabilizer. Other stabilizer can be substituted. The resulting composition can be used as is or diluted with distilled water as a fish preservative and applied to the skin of the fish. This would be fish at room temperature that can be preserved for weeks without refrigeration.

The composition can also be added with effective dermatological creams, and without dilution to retard or destroy melanoma cancer cells on human skin.

Example 2

The composition as shown in Example 1 can be altered by the substitution of urea for the ammonium sulfate in the amount of 46 percent active urea. The remainder of the methodology will be the same.

It is believed that numerous applications as a bactericide, a fungicide, a viricide or other active acidic cleaning agent can be used for the compound at extremely low pHs (below 2), while at the same time the composition is not an irritant or deleterious to healthy human cells.

The following is an alternate embodiment of the invention.

The mixture shall consist of sulfuric acid, water and ammonium sulfate, or substitute 46 percent urea for the 21 percent ammonium sulfate.

One pound of 21 percent ammonium sulfate for gallon of water up to 5 pounds of 21 percent ammonium sulfate per gallon of water (distilled) with the ratio of water and ammonium sulfate to the sulfuric acid being from a 1 to 1 mixture up to a 5 to 1 mixture with the higher number being the water and ammonium sulfate mixture. Mixtures ratios are by weight.

Temperature ranges are from approximately 300° F. and not to exceed approximately 1200° F., preferably between approximately 350° F. and approximately 500° F. for consistency of the finished product. Pressures range from approximately 5 PSI to approximately 800 PSI and DC voltage ranges from approximately 1 amp to approximately 100 amps.

There are 4 things that affect the rate of reaction of the invention: temperature, pressure, amperage, and the amount of product being used. These are four variables that determine how long the process takes.

Example 3

Sulfuric acid, preferably around 98% purity, is placed in container in a predetermined quantity.

The next step is to place distilled water in a separate container and heat the water to approximately 140° F. at which time 2.77 pounds per gallon of 21 percent active ammonium sulfate is added to the water using a 316 L stainless tube to inject air to dissolve the ammonium sulfate in the water.

Simultaneously, the $H_2SO_4$, and the $H_2O$, and the ammonium sulfate $(NH_4)_2SO_4$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture to dynamically rotate with the pressure vessel.

Two electrodes, a cathode and an anode provide a DC voltage one foot above the bottom of the container at approximately 3 amps with the electrodes being three feet apart.

The mixture is heated to 800° F. and maintained at that temperature for three to four hours during which time excess hydrogen gas is removed.

After four hours, the mixture is allowed to return and cool down to room temperature. After cool down, an additional lot of the same mixture, is reintroduced into the original cool down mixture to act as a stabilizer. The resulting composition can be used as is or diluted with distilled water as a fish preservative and applied to the skin of the fish.

Example 4

Using the same process as described in Example 3, phosphoric acid, preferably around 98% purity, is placed in container in a predetermined quantity, such as approximately 1 gallon to approximately 2 gallon ratio with the water.

The next step is to place distilled water in a separate container and heat the water to approximately 140° F. at which time approximately 1 lb. to approximately 3 lbs. per to gallon of sodium sulfate is added to the water using a mechanical mixer to dissolve the sodium sulfate in the water.

Simultaneously, the phosphoric acid, and the $H_2O$, and the sodium sulfate $(Na_2SO_4)$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture to dynamically rotate with the pressure vessel.

Two electrodes, a cathode and an anode provide a DC voltage one foot above the bottom of the container at approximately 3 amps with the electrodes being three feet apart.

The mixture is heated to approximately 350° F. and maintained at that temperature for three to four hours during which time excess hydrogen gas is removed.

After four hours, the mixture is allowed to cool down to room temperature. After cool down, an additional lot (10-15 weight percent) of the original mixture of acid, water and sodium sulfate, is reintroduced into the cooled reaction mixture to act as a stabilizer. The resulting composition can be used as is or diluted with distilled water for a spray or wash to be applied to fowl held in open pens.

Example 5

When the low pH acidic composition of the present invention is prepared (with electrolysis) in accordance with the procedure in Example 1 and sodium sulfate is substituted for ammonium sulfate, the resulting composition is very compatible with the use of chlorine solutions in the treatment of water and waste water. Also, when the use of direct current (DC) is omitted from the process of Example 1 (without electrolysis), the product with sodium sulfate is equally effective and compatible with processes using chlorine for water treatment. In Table II below, there are results of chlorine compatibility tests using the low pH acidic composition of the present invention, made with sodium sulfate, with and without electrolysis.

TABLE II

Chlorine Compatibility Tests of Low pH Acidic
Composition made with Sodium Sulfate Test #1 - 1 ppm Chlorine, 1 ppm copper
(Acid, Water, Sodium Sulfate - w/ electrolysis)

| Time (minutes) | Soln 1 (ppm) | Soln 2 (ppm) | |
| --- | --- | --- | --- |
| 0 | 1.08 | 1.08 | Starting FAC* |
| 15 | 1.09 | 1.09 | |
| 30 | 1.09 | 1.10 | |
| 45 | 1.08 | 1.08 | No |
| 60 | 1.09 | 1.08 | Reduction |

Test #2 - 2 ppm Chlorine, 1 ppm copper
(Acid, Water, Sodium Sulfate - w/ electrolysis)

| Time (minutes) | Soln 1 (ppm) | Soln 2 (ppm) | |
| --- | --- | --- | --- |
| 0 | 1.99 | 1.99 | Starting FAC* |
| 15 | 2.00 | 2.02 | |
| 30 | 2.04 | 2.03 | |
| 45 | 2.03 | 2.02 | No |
| 60 | 2.05 | 2.03 | Reduction |

Test #3 - 1 ppm Chlorine, 1 ppm copper
(Acid, Water, Sodium Sulfate - No electrolysis)

| Time (minutes) | Soln 1 (ppm) | Soln 2 (ppm) | |
| --- | --- | --- | --- |
| 0 | 1.09 | 1.09 | Starting FAC* |
| 15 | 1.08 | 1.09 | |
| 30 | 1.07 | 1.08 | |
| 45 | 1.09 | 1.10 | No |
| 60 | 1.09 | 1.11 | Reduction |

Test #4 - 2 ppm Chlorine, 1 ppm copper
(Acid, Water, Sodium Sulfate - No electrolysis)

| Time (minutes) | Soln 1 (ppm) | Soln 2 (ppm) | |
| --- | --- | --- | --- |
| 0 | 2.01 | 2.00 | Starting FAC* |
| 15 | 2.02 | 2.02 | |
| 30 | 2.03 | 2.04 | |
| 45 | 2.04 | 2.02 | No |
| 60 | 2.02 | 2.00 | Reduction |

* FAC = Free Available Chlorine

The first set of data (Tests #1 and #2) use the low pH acidic composition made with electrolysis at a 1 ppm copper dosage and chlorine at 1 and 2 ppm. This data shows that there are no significant reductions in chlorine over the 1 hour test period. The second set of data (Tests #3 and #4) use the low pH acidic composition made without electrolysis at 1 ppm copper dosage and chlorine at 1 ppm and 2 ppm. This data again shows that there are no significant reductions in chlorine over the 1 hour test period.

Thus, the tests show that there is no incompatibility between the low pH acidic composition made with sodium sulfate and chlorine and could be used in conjunction with chlorine for disinfecting water and waste water. The data demonstrate that electrolysis does not negatively affect the product's compatibility with chlorine, perhaps producing other oxidizing substances such as, hydrogen peroxides, peroxysulfates and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An acidic composition of matter that is effective in the destruction of microorganisms and is not an irritant, produced by the process of:
    combining an acid selected from the group consisting of phosphoric acid, fumaric acid and acetic acid with water and a metallic sulfate selected from the group consisting of sodium sulfate, magnesium sulfate, zinc sulfate, manganese sulfate, and copper sulfate to provide a mixture (III);
    combining the mixture (III) in a pressurized vessel at a pressure that is 15 psi above atmospheric pressure and heating the mixture to temperatures in a range between approximately 250° F. and approximately 1200° F. to form mixture (IV);
    cooling the mixture (IV); and
    adding a stabilizer consisting of 10 weight percent to approximately 15 weight percent of mixture (III) to the cooled mixture (IV), providing a stable composition having a pH value below 2.

2. The composition of claim 1, wherein the water is selected from the group consisting of distilled water, deionized water, filtered water, pharmaceutical or medical grade water.

3. A method of preparing an acidic composition of matter that is effective in the destruction of microorganisms and is not an irritant, produced by the process of:
    (a) adding an acid of approximately 98% purity selected from at least one of: phosphoric acid, fumaric acid, and acetic acid to a first container;
    (b) heating water;
    (c) mixing at least one compound selected from at least one of an ammonium compound, and a metallic sulfate in said heated water;
    (d) simultaneously combining the mixture of the acid, heated water, and at least one of an ammonium compound, and metallic sulfate to form mixture (V);
    (e) adding mixture (V) to a separate pressurized vessel maintained at a pressure that is 15 psi above atmospheric pressure;
    (f) heating the pressurized mixture (V) to temperatures in a range between approximately 250° F. and approximately 1200° F., at a pressure that is 15 psi above atmospheric pressure; and
    (g) cooling said mixture and adding a stabilizer consisting of 10 weight percent to approximately 15 weight percent of mixture (V) of step (d) to the cooled mixture providing a stable composition having a pH value below 2.

4. The method of claim 3, wherein the water is selected from the group consisting of: distilled water, deionized water, filtered water, pharmaceutical or medical grade water.

5. The method of claim 3, wherein the heating step includes the step of: heating the water in a ratio of approximately twice the volume of said acid in the separate container to approximately 140 degrees Fahrenheit.

6. The method of claim 3, wherein the at least one of an ammonium compound and metallic sulfate is mixed at a ratio of approximately 1 lb. to approximately 3 lbs. of the ammonium compound per gallon of water and approximately 1 lb. to approximately 3 lbs. of the metallic sulfate per gallon of water.

7. The method of claim 3, wherein the step of the simultaneously combining includes the step of: simultaneously combining the mixture of the acid, the heated water, and at least one of an ammonium compound or metallic sulfate to form mixture (V) that is added to the separate pressurized vessel by injection.

8. The method of claim 7, further including the steps of: heating the pressurized vessel to approximately 800 degrees Fahrenheit for approximately 3 hours, then cooling the heated mixture prior to adding the stabilizer in an amount of approximately 10 weight percent of the cooled mixture.

9. The method of claim 3, wherein the metallic sulfate is selected from the group consisting of sodium sulfate, magnesium sulfate, zinc sulfate, manganese sulfate, and copper sulfate.

\* \* \* \* \*